(12) United States Patent
Semizarov et al.

(10) Patent No.: US 9,297,045 B2
(45) Date of Patent: *Mar. 29, 2016

(54) DIAGNOSTIC METHODS FOR DETERMINING PROGNOSIS OF NON-SMALL CELL LUNG CANCER

(75) Inventors: Dimitri Semizarov, Chicago, IL (US); Xin Lu, Libertyville, IL (US); Ke Zhang, Grand Forks, ND (US); Rick R. Lesniewski, Collegeville, PA (US); John S. Coon, Oak Park, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/910,892

(22) Filed: Oct. 25, 2010

(65) Prior Publication Data

US 2011/0130295 A1    Jun. 2, 2011

Related U.S. Application Data

(60) Provisional application No. 61/254,955, filed on Oct. 26, 2009.

(51) Int. Cl.
*C12Q 1/68* (2006.01)
(52) U.S. Cl.
CPC ........ *C12Q 1/6886* (2013.01); *C12Q 2600/106* (2013.01); *C12Q 2600/112* (2013.01); *C12Q 2600/118* (2013.01); *C12Q 2600/156* (2013.01)
(58) Field of Classification Search
CPC ...... C12A 1/6886; C12A 1/68; C12A 1/6813; C12A 1/6876; C12Q 600/156; C12Q 2600/178; C12Q 2600/156; C12Q 2600/118; G01N 33/57423; G01N 2800/56; G01N 2800/52; G01N 2600/118; G01N 2600/156
See application file for complete search history.

(56) References Cited

U.S. PATENT DOCUMENTS 4,683,195 A    7/1987   Mullis et al.
4,683,202 A    7/1987   Mullis
(Continued)

FOREIGN PATENT DOCUMENTS

CN    1384207 A    12/2002
EP    320308 A2    6/1989
(Continued)

OTHER PUBLICATIONS

Muller et al., Cyclin E is the Only Cyclin-dependent Kinase 2-associated Cyclin that Predicts Metastasis and Survival in Early Stage Non-Small Cell Lung Cancer, Cancer Research 61, 647-653, Jan. 15, 2001.*

(Continued)

*Primary Examiner* — Reza Ghafoorian
(74) *Attorney, Agent, or Firm* — Lisa V. Mueller; Michael Best & Friedrich LLP

(57) ABSTRACT

Disclosed are methods for identifying early-stage non-small-cell lung cancer (NSCLC) patients who will have an unfavorable prognosis for the recurrence of lung cancer after surgical resection. The methods are based in part on the discovery that chromosomal copy number gains at Chr19, 34.7 Mb-35.6 Mb can be used for prognostic classification. The methods preferably use fluorescence in situ hybridization with fluorescently labeled nucleic acid probes to hybridize to patient samples to quantify the chromosomal copy number of this genetic locus.

9 Claims, 1 Drawing Sheet

(56) References Cited

U.S. PATENT DOCUMENTS

| | | | |
|---|---|---|---|
| 5,322,770 | A | 6/1994 | Gelfand |
| 5,491,224 | A | 2/1996 | Bittner et al. |
| 5,756,696 | A | 5/1998 | Gray et al. |
| 5,776,688 | A | 7/1998 | Bittner et al. |
| 6,174,681 | B1 | 1/2001 | Halling et al. |
| 7,897,329 | B2 | 3/2011 | Nakamura et al. |
| 2003/0087248 | A1 | 5/2003 | Morrison et al. |
| 2006/0024692 | A1 | 2/2006 | Nakamura et al. |
| 2006/0063194 | A1 | 3/2006 | Morrison et al. |

FOREIGN PATENT DOCUMENTS

| | | | |
|---|---|---|---|
| EP | 439182 B1 | | 4/1996 |
| WO | WO 2006/128195 | * | 5/2005 |
| WO | WO2005117553 A2 | | 12/2005 |
| WO | WO2006128195 A2 | | 11/2006 |
| WO | 2007055553 A1 | | 5/2007 |
| WO | 2008050356 A1 | | 5/2008 |
| WO | 2009129154 A1 | | 10/2009 |

OTHER PUBLICATIONS

Hirsch et al., Epidermal Growth Factor Receptor in Non-Small-Cell Lung Carcinomas: Correlation Between Gene Copy Number and Protein Expression and Impact on Prognosis, Journal of Clinical Oncology, vol. 21, No. 20 Oct. 15, 2003: pp. 3798-3807.*

Schraml et al., Cyclin E overexpression and amplification in human tumours, J Pathol 2003; 200: 375-382.*

Erlanson et al., Expression of Cyclin E and the Cyclin-Dependent Kinase Inhibitor p27 in Malignant Lymphomas-Prognostic Implications, Blood, vol. 92, No. 3 Aug. 1, 1998: pp. 770-777.*

Leung et al., Comprehensive analysis of 19q12 amplicon in human gastric cancers, Modern Pathology (2006) 19, 854-863.*

ELF® 97 mRNA In Situ Hybridization Kits, Product Information, by Molecular Probes, Revised: Feb. 2, 2001, MP 06604.*

Blons et al., Genome wide SNP comparative analysis between EGFR and KRAS mutated NSCLC and characterization of two models of oncogenic cooperation in non-small cell lung carcinoma, BMC Medical Genomics 2008, 1:25.*

Scott et al., Treatment of Non-small Cell Lung Cancer Stage I and Stage II ACCP Evidence-Based Clinical Practice Guidelines. Chest,132, 3, Sep. 2007 Supplement, pp. 234S-242S.*

Scott, Treatment of Non-small Cell Lung Cancer Stage I and Stage II, Chest,132:3, Sep. 2007 Supplement, pp. 234S-242S.*

Cappuzzo F., et al., "Increased MET Gene Copy Number Negatively Affects Survival of Surgically Resected Non-Small-Cell Lung Cancer Patients," Journal of Clinical Oncology, 2009, vol. 27 (10), pp. 1667-1674.

Etemadmoghadam D., et al., "Integrated Genome-Wide DNA Copy Number and Expression Analysis Identifies Distinct Mechanisms of Primary Chemoresistance in Ovarian Carcinomas," Clinical Cancer Research, 2009, vol. 15 (4), pp. 1417-1427.

Freier K., et al., "Recurrent Copy Number Gain of Transcription Factor SOX2 and Corresponding High Protein Expression in Oral Squamous Cell Carcinoma," Genes, Chromosomes and Cancer, 2010, vol. 49 (1), pp. 9-16.

Halling K.C., et al., "Fluorescence In Situ Hybridization in Diagnostic Cytology," Human Pathology, 2007, vol. 38, pp. 1137-1144.

International Search Report and Written Opinion for Application No. PCT/US2010/053900 , mailed on Feb. 11, 2011, 12 pages.

Leung S.Y., et al., "Comprehensive Analysis of 19q12 Amplicon in Human Gastric Cancers," Modern Pathology, 2006, vol. 19 (6), pp. 854-863.

Marone M., et al., "Analysis of Cyclin E and CDK2 in Ovarian Cancer: Gene Amplification and RNA Overexpression," International Journal of Cancer, 1998, vol. 75, pp. 34-39.

Marshall R.L., et al., "Detection of HCV RNA by the Asymmetric Gap Ligase Chain Reaction," PCR Methods and Applications, 1994, vol. 4 (2), pp. 80-84.

Matsuzaki H., et al., "Genotyping Over 100,000 SNPs on a Pair of Oligonucleotide Arrays," Nature Methods, 2004, vol. 1 (2), pp. 109-111.

Mishina T., et al., "Cyclin E Expression, a Potential Prognostic Marker for Non-Small Cell Lung Cancers," Clinical Cancer Research, 2000, vol. 6 (1), pp. 11-16.

Morrison, L.E. et al., "Labeling Fluorescence In Situ Hybridization Probes for Genomic Targets," Methods in Molecular Biology, 2002, vol. 204, pp. 21-40.

Nakayama K., et al., "Amplicon Profiles in Ovarian Serous Carcinomas," International Journal of Cancer, 2007, vol. 120 (12), pp. 2613-2617.

Nath J., et al., "Fluorescence in Situ Hybridization (FISH): DNA Probe Production and Hybridization Criteria," Biotechnic & Histochemistry, 1997, vol. 73 (1), pp. 6-22

Peng W.X., et al., "Array-Based Comparative Genomic Hybridization Analysis of High-Grade Neuroendocrine Tumors of the Lung," Cancer Science, 2005, vol. 96 (10), pp. 661-667.

Singhal S., et al., "Prognostic Implications of Cell Cycle, Apoptosis, and Angiogenesis Biomarkers in Non -Small Cell Lung Cancer: A Review," Clinical Cancer Research, 2005, vol. 11 (11), pp. 3974-3986.

Wheeless L.L., et al., "Bladder Irrigation Specimens Assayed by Fluorescence In Situ Hybridization to Interphase Nuclei," Cytometry, 1994, vol. 17 (4), pp. 319-326.

Yasmeen A., et al., "E- and A-Type Cyclins as Markers for Cancer Diagnosis and Prognosis," Expert Review of Molecular Diagnostics, 2003, vol. 3, (5), pp. 617-633.

Broet P., et al., "Prediction of Clinical Outcome in Multiple Lung Cancer Cohorts by Integrative Genomics: Implications for Chemotherapy Selection," Cancer Research, 2009, vol. 69 (3), pp. 1055-1062.

Chen L., et al., "Lysine Acetyltransferase GCN5 Potentiates the Growth of Non-Small Cell Lung Cancer Via Promotion of E2F1, Cyclin D1, and Cyclin E1 Expression," Journal of Biological Chemistry, 2013, vol. 288 (20), pp. 14510-14521.

Final Office Action mailed Jul. 31, 2013 for U.S. Appl. No. 12/910,891, filed Oct. 25, 2010.

Galimberti F., et al., "Targeting the Cyclin E-Cdk-2 Complex Represses Lung Cancer Growth by Triggering Anaphase Catastrophe," Clinical Cancer Research, 2010, vol. 16 (1), pp. 109-120.

Huang L.N., et al., "Meta-Analysis for Cyclin E in Lung Cancer Survival," Clinical Chimica Acta, 2012, vol. 413 (7-8), pp. 663-668.

International Preliminary Report on Patentability for Application No. PCT/US2010/053893, mailed on May 1, 2012, 1 page.

International Preliminary Report on Patentability for Application No. PCT/US2010/053900, mailed on May 1, 2012, 1 page.

International Search Report and Written Opinion for Application No. PCT/US2010/053893, mailed on Jun. 10, 2011, 12 pages.

Invitation to Pay Additional Fees for Application No. PCT/US2010/053893, mailed on Mar. 28, 2011, 6 pages.

Kim T.M., et al., "Genome-Wide Screening of Genomic Alterations and their Clinicopathologic Implications in Non-Small Cell Lung Cancers," Clinical Cancer Research, 2005, vol. 11 (23), pp. 8235-8242.

Non-Final Office Action mailed Oct. 12, 2012 for U.S. Appl. No. 12/910,891, filed Oct. 25, 2010.

Non-Final Office Action mailed Jan. 29, 2014 for U.S. Appl. No. 12/910,891, filed Oct. 25, 2010.

Non-Final Office Action mailed Jul. 9, 2014 for U.S. Appl. No. 12/910,891, filed Oct. 25, 2010.

Aviel-Ronen S., et al., "Genomic Markers for Malignant Progression in Pulmonary Adenocarcinoma with Bronchioloalveolar Features," Proceedings of the National Academy of Sciences, USA, 2008, vol. 105 (29), pp. 10155-10160.

Final Office Action mailed Jan. 2, 2015 for U.S. Appl. No. 12/910,891, filed Oct. 25, 2010.

Muller K.M., et al., "New Aspects of Lung Tumor Pathology," Verhandlungen Der Deutschen Gesellschaft Fur Pathologie, 1999, vol. 83, pp. 168-183.

Non-Final Office Action mailed May 7, 2015 for U.S. Appl. No. 12/910,891, filed Oct. 25, 2010.

(56) References Cited

OTHER PUBLICATIONS

Wrage M., et al., "Genomic Profiles Associated With Early Micrometastasis in Lung Cancer: Relevance of 4q Deletion," Clinical Cancer Research, 2009, vol. 15 (5), pp. 1566-1574.

Zhao X., et al., "Homozygous Deletions and Chromosome Amplifications in Human Lung Carcinomas Revealed by Single Nucleotide Polymorphism Array Analysis," Cancer Research, 2005, vol. 65 (13), pp. 5561-5570.

* cited by examiner

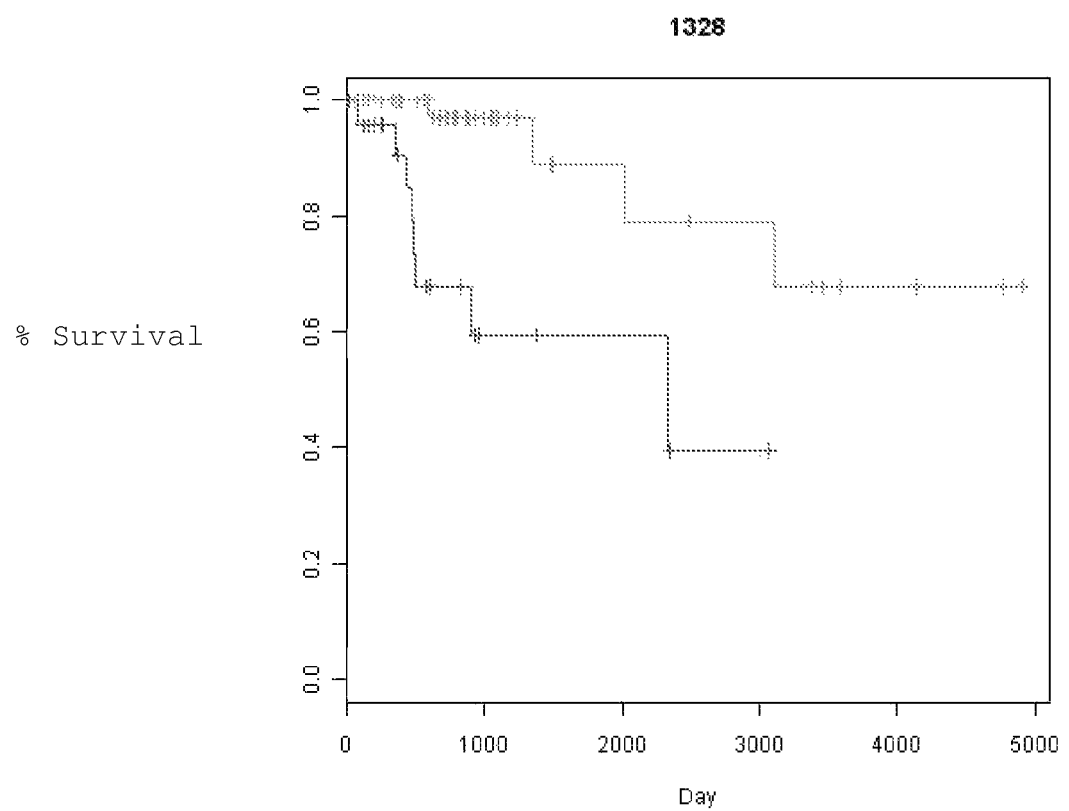

DIAGNOSTIC METHODS FOR DETERMINING PROGNOSIS OF NON-SMALL CELL LUNG CANCER

CROSS REFERENCE TO A RELATED APPLICATION

This application claims priority from U.S. provisional patent application No. 61/254,955, filed on Oct. 26, 2009, the disclosure of which is herein incorporated by reference in its entirety.

FIELD OF THE INVENTION

The present disclosure relates to in vitro diagnostic assays of tissue samples from lung cancer patients for determining patient prognosis, and in particular relates to an in vitro assay for determining prognosis of early stage patients, such as those diagnosed with Stage I or Stage II non-small-cell lung cancer.

BACKGROUND OF THE INVENTION

Lung cancer accounted for almost one third of cancer deaths in the United States in 2005, and is broadly classified into two types: non-small-cell lung cancer and small cell lung cancer. Non-small-cell lung cancer (NSCLC) comprises 80-85% of lung cancer cases in the United States. The types of NSCLC are named for the kinds of cells found in the cancer and how the cells look under a microscope. NSCLC comprises three major types: (i) Squamous cell carcinoma, which begins in squamous cells, that are thin, flat cells that look like fish scales. Squamous cell carcinoma is also called epidermoid carcinoma; (ii) Large cell carcinoma, which begins in several types of large lung cells; (iii) Adenocarcinoma, which begins in the cells that line the alveoli of the lung and make substances such as mucus. Other less common types of NSCLC include pleomorphic carcinoma, carcinoid tumor and unclassified carcinoma.

Diagnosis of NSCLC is done by a pathologist's examination of suspected tissue, such as a biopsy sample. After NSCLC diagnosis, the patient's disease is assigned a prognosis (the chance of recovery) using the patient's overall health and age, the severity of symptoms such as coughing and difficulty in breathing, the particular type of NSCLC, and the staging of the cancer. Staging takes into account the size of the tumor and whether the tumor is present in the lung only or has spread to other places in the body. The particular treatment options for a NSCLC patient are then selected based upon these considerations, and the cancer staging is an important component for treatment selection. Patients with early stage NSCLC can be potentially be cured by surgical resection to remove the tumor, but the current diagnostic modalities are not able to predict which patients will recur after surgery. Cancer is a frequently fatal disease with a low cure rate, for which the majority of treatments are directed at improving the quality and duration of life. Because cancer cells are human cells, frequently distinguished only by the accumulation of a relatively small number of genetic aberrations or protein mutations, drug therapies that are useful in killing cancer cells are commonly also detrimental to many normal human cells and cause typically significant toxicities in patients who are treated. Furthermore, because cancers frequently recur locally or metastasize to tissues and organs remote from their tissue of origin, it is critical to know which patients with early stage cancers need drug treatment after surgical removal of their primary tumor. This is an especially critical issue in patients with early stage NSCLC, whose tumors were detected early and removed surgically, specifically patients with Stage I and IIA disease. Under-treating these patients with anti-cancer drugs results in an unacceptably high rate of patients developing recurrent or metastatic disease, ultimately leading to increased morbidity and death. Over-treating this population results in an unacceptably high rate of patients who do not need drug therapy experiencing the toxic side effects from the drugs given to them.

The National Comprehensive Cancer Network internet web site describes NSCLC staging as follows. "The system most often used in United States clinical practice to describe the growth and spread of non-small-cell lung cancer (NSCLC) is the TNM staging system, also known as the American Joint Committee on Cancer (AJCC) system. In TNM staging, information about the tumor (T), any spread into nearby lymph nodes (N), and any distant organ metastases (M) is combined and a stage is assigned to specific TNM groupings. The grouped stages are described using the number 0 and Roman numerals from I to IV.

"T categories are based on the lung cancer's size, its spread and location within the lungs, and its spread to nearby tissues. In the T is category, the cancer is found only in the layer of cells lining the air passages. It has not spread into other lung tissues. This category is also known as carcinoma in situ.

"In the T1 category, the cancer is no larger than 3 centimeters (slightly less than 1 to 1¼ inches), has not spread to the visceral pleura (membranes that surround the lungs), and does not affect the main branches of the bronchi.

"In the T2 category, the cancer has one or more of the following features: (i) it is larger than 3 cm; (ii) it involves a main bronchus of a lung but is not closer than 2 cm (about 3¼ to 4 inches) to the point where the trachea (windpipe) branches into the left and right main bronchi; or (iii) has spread to the visceral pleura. The cancer may partially block the airways, but this has not caused the entire lung to collapse or develop pneumonia.

"In the T3 category, the cancer has one or more of the following features: (i) it has spread to the chest wall, the diaphragm (the breathing muscle that separates the chest from the abdomen), the mediastinal pleura (the membranes surrounding the space between the 2 lungs), or parietal pericardium (the membranes of the sac surrounding the heart); (ii) it involves a main bronchus of a lung, and it is closer than 2 cm (about 3¼ inch) to the point where the trachea (or windpipe) branches into the left and right main bronchi, but does not involve this area; or (iii) It has grown into the airways enough to cause one lung to entirely collapse or to cause pneumonia of the entire lung.

"In the T4 category, the cancer has one or more of the following features: (i) It has spread to the mediastinum (the space behind the chest bone and in front of the heart), the heart, the trachea (windpipe), the esophagus (the tube connecting the throat to the stomach), the backbone, or the point where the trachea branches into the left and right main bronchi; (ii) Two or more separate tumor nodules are present in the same lobe; or (iii) a malignant pleural effusion is present, which is the existence of fluid containing cancer cells in the space surrounding the lung.

"The N category depends on which, if any, of the lymph nodes near the lungs are affected by the cancer. In the N0 category, the cancer has not spread to any lymph node. In the N1 category, the cancer has spread to lymph nodes within the lung or into the hilar lymph nodes (those located around the area where the bronchus enters the lung). In N1 category the affected lymph nodes are only on the same side as the cancerous lung. In the N2 category, the cancer has spread to subcarinal lymph nodes (those which are around the point where the trachea branches into the left and right bronchi) or to lymph nodes in the mediastinum (the space behind the chest bone and in front of the heart). In the N2 category, the affected lymph nodes are on the same side of the cancerous lung. In the N3 category, the cancer has spread to lymph nodes near the collarbone on either side, and/or to the hilar or mediastinal lymph nodes on the side opposite the cancerous lung.

"The M category depends on whether the cancer has metastasized and spread to any distant tissues and organs. In the M0 category, there is no distant cancer spread. In the M1 category, the cancer has spread to 1 or more distant sites. Sites which are considered distant include other lobes of the lungs, lymph nodes further than those used to determine the N category of the cancer, and other organs or tissues such as the liver, bones, or brain.

Once the T, N, and M categories have been assigned for the particular NSCLC, this information is combined (stage grouping) to assign an overall stage of 0, I, II, III, or IV (see Table 1). Various combinations of the T and N categories are combined into stages. The stages identify tumor types that have a similar prognosis and are treated in a similar way. As noted in Table 1, a tumor with distant spread (i.e., an M1 category cancer) is considered Stage 1V, regardless of tumor size of involvement of lymph nodes." The following Table from the NCCN internet web site shows the combined category and stage classification for NSCLC.

TABLE 1

| Overall Stage | T Category | N Category | M Category |
|---|---|---|---|
| Stage 0 | Tis | N0 | M0 |
| Stage IA | T1 | N0 | M0 |
| Stage IB | T2 | N0 | M0 |
| Stage IIA | T1 | N1 | M0 |
| Stage IIB | T2 | N1 | M0 |
|  | T3 | N0 | M0 |
| Stage IIIA | T1 | N2 | M0 |
|  | T2 | N2 | M0 |
|  | T3 | N1 | M0 |
|  | T3 | N2 | M0 |
| Stage IIIB | Any T | N3 | M0 |
|  | T4 | Any N | M0 |
| Stage IV | Any T | Any N | M1 |

NSCLC patients with lower stage numbers generally have a more favorable prognosis and outlook for survival, and these patients are generally treated by surgical resection of the tumor. However, even for early stage patients, such as those with Stage 1B, Stage IIA or IIB NSCLC, a significant percentage of these patients will recur after surgical resection with more aggressive disease and die. The current clinical diagnostic methods are incapable of identifying early stage NSCLC prognosis with sufficient accuracy to direct more aggressive therapy against those patients more likely to recur. Better in vitro diagnostic methods to identify higher risk, early stage NSCLC patients who should receive neoadjuvant or adjuvant chemotherapy or even forgo surgical resection altogether, are therefore needed.

Molecular in vitro diagnostic assays based on fluorescence in situ hybridization (FISH) using fluorescently labeled DNA hybridization probes to identify chromosomal abnormalities have been disclosed for use in the selection of chemotherapy for NSCLC patients, (PCT/US2005/018879, "Methods for prediction of clinical outcome to epidermal growth factor inhibitors by cancer patients", M. Garcia et al.). FISH assays have been described as an initial diagnostic assay for NSCLC in U.S. Patent Application 20060063194, "Methods and probes for the detection of cancer", L. Morrison et al., published Mar. 23, 2006 (hereafter referred to as "Morrison '194"), the disclosure of which is incorporated herein by reference in its entirety. The Morrison '194 application describes multiple FISH probe sets useful for screening and diagnosis of NSCLC, and one probe set described in Morrison '194 is commercially available as the LAVysion™ probe set from Abbott Molecular, Inc. (Des Plaines, Ill., U.S.A.) under ASR (Analyte Specific Reagent) labeling for use by clinical laboratories to produce clinical diagnostic assays. Under the U.S. Food and Drug Administration ASR labeling requirements, the ASR labeling must not include any claims as to the medical utility of the ASR. The LAVysion ASR probe set comprises four FISH probes: a chromosome 5p15 locus specific probe labeled with the SpectrumGreen green fluorophore, a chromosome 8q24 locus specific probe labeled with the SpectrumGold yellow fluorophore, a chromosome 6 enumeration probe labeled with the SpectrumAqua blue fluorophore, and a chromosome 7p12 locus specific probe labeled with the SpectrumRed red fluorophore. Research performed using the LAVysion probe set has been described and is reviewed for example in K. Halling et al., "Fluorescence in situ hybridization in diagnostic cytology", Hum. Path. (2007) 38: 1137-1144.

Overexpression of cyclin E has previously been associated with poor outcome in lung cancer (reviewed in Singhal et al., Clin. Cancer Res., 2005, 11, pp. 3974-3986). Amplification of cyclin E has also been associated with ovarian cancer. (M. Marone et al., Internat'l J. Cancer, 1998, 75, pp. 34-39). However, no copy number alterations at the cyclin E locus have been established as predictive markers. Moreover, no previous reports on FISH assays for NSCLC have disclosed the use of FISH probes to more accurately identify prognosis for early stage NSCLC, in particular, those classified as Stage I or Stage II.

SUMMARY OF THE INVENTION

In one aspect, the present disclosure provides a method of predicting disease outcome in a patient being treated for lung cancer, the method comprising the steps of a) providing a test sample from a patient; b) determining a copy number for the cyclin E1 gene in the test sample; c) comparing the copy number of the cyclin E1 gene in the test sample against a baseline copy number of two, thereby determining the presence or absence of a copy number gain for the cyclin E1 gene in the test sample; and d) based on the presence or absence of a copy number gain for the cyclin E1 gene in the test sample, identifying the patient as having an increased risk of a poor disease outcome when compared to a baseline measure of disease outcome in patients having no copy number gain in the cyclin E1 gene, wherein the presence of a copy number gain in the cyclin E1 gene is predictive of poor disease outcome. The poor disease outcome is at least one of a decreased overall survival time when compared to an overall survival time of patients having no copy number gain for the cyclin E1 gene, and a shorter time to recurrence when compared to an overall survival time of patients having no copy number gain for the cyclin E1 gene.

In another aspect, the present disclosure provides a method of predicting disease outcome in a patient being treated for lung cancer, the method comprising the steps of a) providing a test sample from a patient; b) determining the presence or absence of a copy number gain for the cyclin E1 gene; and c) based on the presence or absence of a copy number gain for the cyclin E1 gene, determining whether the patient has a higher risk of a decreased overall survival time or a shorter time to recurrence when compared to an overall survival time of patients having no copy number gain for the cyclin E1 gene.

In any of the methods, the cyclin E1 gene is located within the region of chromosome 19 at 34.7 Mb-35.6 Mb. In any of the methods, the test sample can be a tissue sample that may contain tumor cells, such as for example a blood sample, a tumor tissue or a suspected tumor tissue, a thin layer cytological sample, a fine needle aspirate sample, a lung wash sample, a pleural effusion sample, a fresh frozen tissue sample, a paraffin embedded tissue sample or an extract or processed sample produced from any of the preceding. In an exemplary embodiment, the tissue sample is a lung tissue sample or a peripheral blood sample comprising circulating tumor cells. The determining step (b) can be performed, for example, by in situ hybridization, such as with a nucleic acid probe that is fluorescently labeled, using at least two nucleic acid probes, or with a peptide nucleic acid probe. The determining step (b) can be performed by polymerase chain reaction, a nucleic acid sequencing assay, or a nucleic acid microarray assay. In an exemplary embodiment, the lung cancer is non-small-cell lung cancer, such as for example, any of squamous cell carcinoma, large cell carcinoma and adenocarcinoma. The patient may be treated with chemotherapy, radiation, surgery or any combination thereof.

In another aspect, the present disclosure provides a method of selecting a treatment for a patient suffering from lung cancer, the method comprising the steps of: a) providing a test sample from the patient wherein treatment with a chemotherapy agent is at least one treatment option for the patient; b) determining a copy number for the cyclin E1 gene in the test sample; c) comparing the copy number for the cyclin E1 gene in the test sample against a baseline copy number of two, thereby determining the presence or absence of a copy number change for the cyclin E1 gene in the test sample; and d) determining a chemotherapy treatment regimen based on the comparison in step c). The step of determining a treatment regimen based on the comparison in step c) includes for example selecting a chemotherapy agent and determining a frequency of chemotherapy treatment when a copy number change is present for the cancer outcome marker. The test sample is for example a tissue sample that may contain tumor cells, such as a blood sample, a tumor tissue or a suspected tumor tissue, a thin layer cytological sample, a fine needle aspirate sample, a lung wash sample, a pleural effusion sample, a fresh frozen tissue sample, a paraffin embedded tissue sample or an extract or processed sample produced from any of a peripheral blood sample, and in an exemplary embodiment is a lung tissue sample or a peripheral blood sample with circulating tumor cells. The determining step (b) can be performed, for example, by in situ hybridization, such as with a nucleic acid probe that is fluorescently labeled, using at least two nucleic acid probes, or with a peptide nucleic acid probe. The determining step (b) can be performed by polymerase chain reaction, a nucleic acid sequencing assay, or a nucleic acid microarray assay. In an exemplary embodiment, the lung cancer is non-small-cell lung cancer, such as for example, any of squamous cell carcinoma, large cell carcinoma and adenocarcinoma. The patient may be also treated with radiation or surgery or a combination thereof.

In another aspect, the present disclosure provides a method of classifying a patient as having a lung cancer that is resistant to treatment comprising the steps of: a) providing a test sample from a patient; b) determining a copy number for the cyclin E1 gene; c) comparing the copy number for the cyclin E1 gene in the test sample against a baseline copy number of two for the cyclin E1 gene to determine the presence or absence of a copy number gain in the cyclin E1 gene in the patient; and d) classifying the patient as having a lung cancer that is resistant to treatment based on the presence of a copy number gain in the cyclin E1 gene. The test sample is for example a tissue sample, such as a blood sample, a tumor tissue or a suspected tumor tissue, a thin layer cytological sample, a fine needle aspirate sample, a lung wash sample, a pleural effusion sample, a fresh frozen tissue sample, a paraffin embedded tissue sample or an extract or processed sample produced from any of a peripheral blood sample, and in an exemplary embodiment is a lung tissue sample or a peripheral blood sample with circulating tumor cells. The determining step (b) can be performed, for example, by in situ hybridization, such as with a nucleic acid probe that is fluorescently labeled, using at least two nucleic acid probes, or with a peptide nucleic acid probe. The determining step (b) can be performed by polymerase chain reaction, a nucleic acid sequencing assay, or a nucleic acid microarray assay. In an exemplary embodiment, the lung cancer is non-small-cell lung cancer, such as for example, any of squamous cell carcinoma, large cell carcinoma and adenocarcinoma. The patient may be treated with chemotherapy, radiation, surgery or any combination thereof.

In another aspect, the present disclosure provides a kit comprising: a) reagents for determining the presence or absence of a copy number gain for the cyclin E1 gene; and b) instructions for performing the test. In an exemplary embodiment of the kit, the reagents to determine the presence or absence of a copy number gain include detectably-labeled polynucleotides that hybridize to at least a portion of the cyclin E1 gene.

BRIEF DESCRIPTION OF THE DRAWINGS

FIG. 1 is a Kaplan-Meier plot showing the overall survival (OS) in days for a 78 patient cohort with early stage NSCLC, classified by presence or absence of a copy number gain in Chr19, 34.7 Mb-35.6 Mb.

DETAILED DESCRIPTION OF THE INVENTION

Previously described expression-based markers of poor outcome in cancer cannot be measured with FISH, a well-established clinical diagnostic tool. Until now, no gene amplifications/deletions have been identified that can predict disease outcome. The inventors have discovered a copy number gain of a chromosomal sequence, at chromosome 19 at approx. 35 Mb, which contains the gene coding for cyclin E, a key regulator of cell cycle. Moreover, the inventors have determined that the copy number gain is statistically significantly associated with shorter overall survival in stage I-II NSCLC.

Accordingly, the present disclosure provides methods of determining prognosis of early stage non-small-cell lung cancer (NSCLC) in a human by assessing the copy number of chromosomal DNA at Chr19, 34.7 Mb-35.6 Mb (Chr 19, start position: 34722418; end position 35643933, in human genome assembly hg18 (NCBI Build 36; "M1"). This stretch of DNA is known to contain the gene sequence encoding Cyclin E1 (CCNE1) among others. Poorer prognosis was assessed relative to patients having a normal baseline copy number, i.e., two copies, of the marker including CCNE1. Poorer prognosis was found to be associated with a copy number gain in the marker using measures of Overall Survival and Time to Recurrence. The methods are particularly beneficial for providing improved prognostic information for early-stage NSCLC patients and enables improved therapy selection for those early stage NSCLC patients at higher risk of cancer recurrence.

The methods encompass a method for determining prognosis of NSCLC patients classified as early stage cancers, in particular those classified as Stage IA, IB, Stage IIA or Stage IIB (Stage IIA and IIB are collectively referred to as Stage II) using the widely used TNM staging system. Alternate NSCLC staging systems based upon other diagnostic classifications can be used to identify the patients whose tissue sample may be assayed by the present methods. As used herein, an early stage NSCLC refers to a NSCLC tumor that has not spread to more than one lymph node, nor metastasized to any other organ. Early stage NSCLC patients are almost always treated by surgical resection seeking complete tumor removal, yet a significant risk of recurrence exists for these early stage patients even where the tumor is believed to be completely resected. Current diagnostic modalities do not allow accurate prediction of which of these early stage cancers are high risk for recurrence and thus should be treated post-resection with adjuvant chemotherapy or before the resection using neoadjuvant chemotherapy. The methods provide prognostic identification of those early stage patients at higher risk by determining chromosomal copy number in the patient sample.

Thus in one aspect, the methods encompass a method of predicting disease outcome in a patient being treated for lung cancer. A test sample, which is a biological sample from the patient, is provided and a copy number for the cyclin E1 gene in the test sample is determined. The copy number from the test sample is compared against a baseline copy number of two, thereby determining the presence or absence of a copy number gain for the cyclin E1 gene. Based on the presence or absence of a copy number gain for the cyclin E1 gene in the test sample, the patient is identifying as having an increased risk of a poor disease outcome when compared to a baseline measure of disease outcome in patients having no copy number gain in the cyclin E1 gene. The presence of a copy number gain in the cyclin E1 gene, i.e., amplification, is predictive of poor disease outcome. The poor disease outcome is at least one of a decreased overall survival time when compared to an overall survival time of patients having no copy number gain for the cyclin E1 gene, and a shorter time to recurrence when compared to the time to recurrence of patients having no copy number gain for the cyclin E1 gene. The methods also encompass a method of predicting disease outcome in a patient being treated for lung cancer, in which based upon the based on the presence or absence of a copy number gain for the cyclin E1 gene, a determination is made as to whether the patient has a higher risk of a decreased overall survival time or a shorter time to recurrence when compared to an overall survival time of patients having no copy number gain for the cyclin E1 gene.

The methods can also be applied to the problem of selecting a treatment for a patient suffering from lung cancer. For example, the method can include providing a test sample from the patient wherein a chemotherapy agent is at least one treatment option for the patient, determining whether a copy number gain for cyclin E1 is present in the sample, and determining whether the patient should be treated with the chemotherapy agent based on whether a copy number gain is present. Alternatively, the method can include determining a chemotherapy treatment regimen based on the comparison in step c). The step of determining a treatment regimen based on the comparison in step c) includes for example selecting a chemotherapy agent and determining a frequency of chemotherapy treatment when a copy number gain is present for CCNE1 within the M1 sequence at Chr19, 34.7 Mb-35.6 Mb (specifically Chr 19, start position: 34722418; end position 35643933, in human genome assembly hg18 (NCBI Build 36)). For example, a more aggressive chemotherapy regimen including a stronger chemotherapy agent and/or more frequent treatment may be selected when a copy number gain is present for CCNE1. The methods can also be used to classify a patient as having a lung cancer that is resistant to treatment. For example, given a determination that a copy number gain is present in the sample from the patient, the patient is classified as having a lung cancer that is resistant to further treatment. The patient may be being currently treated with chemotherapy, radiation, surgery or any combination thereof, or may be being considered for any one of chemotherapy, radiation, surgery treatment or any combination thereof.

The determining step (b) is performed, for example, using in situ hybridization and, more preferably, fluorescent in situ hybridization (FISH) with fluorescently labeled nucleic acid probes or fluorescently labeled probes comprising nucleic acid analogs. Preferably at least two nucleic acid probes are used. A peptide nucleic acid probe can be used. The determining step (b) can also be performed by polymerase chain reaction, a nucleic acid sequencing assay, or a nucleic acid microarray assay as known in the art.

The testing of early stage NSCLC is preferably done on an appropriate biological sample obtained from the patient, by in situ hybridization. In general, in situ hybridization includes the steps of fixing a biological sample, hybridizing one or more chromosomal probes to target DNA contained within the fixed sample, washing to remove non-specifically bound probe, and detecting the hybridized probe. The in situ hybridization can also be carried out with the specimen cells from the biological sample in liquid suspension, followed by detection by flow cytometry. The method preferably uses a FISH assay with a two probe set comprising a probe specific to Chr19, 34.7 Mb-35.6 Mb to evaluate chromosomal copy number abnormalities in a biological sample from a patient. Preferred FISH probes for use in the methods comprise a pair of probes specific to Chr19, 34.7 Mb-35.6 Mb, which may include any portion of the sequence encoding CCNE1.

The identification of NSCLC prognosis according to the disclosed methods can also be used with other prognostic in vitro diagnostic assays, such as evaluating the expression in the patient sample of suitable proteins CCNE1 and other proteins that are known to be encoded in the M1 marker region. Patients whose samples are found with expression of such proteins in conjunction with an abnormal chromosomal copy number pattern, that is associated with an unfavorable outcome (poor prognosis), may be eligible for more aggressive post-surgery treatment, such as chemotherapy.

Typically for a lung cancer patient the biological sample is a tissue sample such as a peripheral blood sample that contains circulating tumor cells, or a lung tumor tissue biopsy or resection. Other suitable tissue samples include for example a thin layer cytological sample, a fine needle aspirate sample, a lung wash sample, a pleural effusion sample, a fresh frozen tissue sample, a paraffin embedded tissue sample or an extract or processed sample produced from any of a peripheral blood sample. Preferably, the sample has been classified as an early stage cancer, for example, such as any of Stage IA, Stage IB, Stage IIA or Stage IIB, using the TNM staging system.

Probes constructed according to the polynucleotide sequence of the cancer outcome marker M1: (Chr 19, start position: 34722418; end position 35643933, in human genome assembly hg18 (NCBI Build 36)) as described herein can be used in various assay methods to provide various types of analysis. For example, such probes can be used in fluorescent in situ hybridization (FISH) technology to perform chromosomal analysis, including copy number profiling, and used to identify cancer-specific copy number changes in the cancer outcome markers. Probes also can be labeled with radioisotopes, directly- or indirectly-detectable haptens, or fluorescent molecules, and utilized for in situ hybridization studies to evaluate copy number of the cancer outcome markers in tissue specimens or cells.

Probes bind selectively to a target polynucleotide sequence, which is at least a portion of the sequence of M1 as described herein, i.e., a chromosomal region that is amplified in certain individuals. The nucleotide sequences of the cancer outcome markers provided herein, or any portion thereof, may be used to produce probes which can be used in various assays for copy number profiling in test samples. The probes may be designed from conserved nucleotide regions of M1, or from non-conserved nucleotide regions of the of M1, or any portion thereof including genes contained therein and portions thereof. The design of such probes for optimization in assays is readily accomplished by one of average skill in the art. Generally, nucleic acid probes are developed from non-conserved or unique regions when maximum specificity is desired, and nucleic acid probes are developed from conserved regions when assaying for nucleotide regions that are closely related to, for example, different members of a multigene family or in related species like mouse and man.

The polymerase chain reaction (PCR) is a technique for amplifying a desired nucleic acid sequence (target) contained in a nucleic acid or mixture thereof. In PCR, a pair of primers are employed in excess to hybridize to the complementary strands of the target nucleic acid. The primers are each extended by a polymerase using the target nucleic acid as a template. The extension products become target sequences themselves, following dissociation from the original target strand. New primers then are hybridized and extended by a polymerase, and the cycle is repeated to geometrically increase the number of target sequence molecules. PCR is disclosed in U.S. Pat. Nos. 4,683,195 and 4,683,202, which are incorporated herein by reference.

The Ligase Chain Reaction (LCR) is an alternate method for nucleic acid amplification. In LCR, probe pairs are used which include two primary (first and second) and two secondary (third and fourth) probes, all of which are employed in molar excess to target. The first probe hybridizes to a first segment of the target strand, and the second probe hybridizes to a second segment of the target strand, the first and second segments being contiguous so that the primary probes abut one another in 5' phosphate-3' hydroxyl relationship, and so that a ligase can covalently fuse or ligate the two probes into a fused product. In addition, a third (secondary) probe can hybridize to a portion of the first probe and a fourth (secondary) probe can hybridize to a portion of the second probe in a similar abutting fashion. Of course, if the target is initially double stranded, the secondary probes also will hybridize to the target complement in the first instance. Once the ligated strand of primary probes is separated from the target strand, it will hybridize with the third and fourth probes that can be ligated to form a complementary, secondary ligated product. It is important to realize that the ligated products are functionally equivalent to either the target or its complement. By repeated cycles of hybridization and ligation, amplification of the target sequence is achieved. This technique is described more completely in EP-A-320 308 to K. Backman published Jun. 16, 1989 and EP-A-439 182 to K. Backman et al., published Jul. 31, 1991, both of which are incorporated herein by reference.

For amplification of mRNAs, it is within the scope of the present disclosure to reverse transcribe mRNA into cDNA followed by polymerase chain reaction (RT-PCR); or, to use a single enzyme for both steps as described in U.S. Pat. No. 5,322,770, which is incorporated herein by reference; or reverse transcribe mRNA into cDNA followed by asymmetric gap ligase chain reaction (RT-AGLCR) as described by R. L. Marshall et al., PCR Methods and Applications 4:80-84 (1994), which also is incorporated herein by reference.

Chromosomal Probes.

Suitable probes for in situ hybridization techniques fall into three broad groups: chromosome enumeration probes, which hybridize to a chromosomal region and indicate the presence or absence of a chromosome; chromosome arm probes, which hybridize to a chromosomal region and indicate the presence or absence of an arm of a chromosome; and locus specific probes, which hybridize to a specific locus on a chromosome and detect the presence or absence of a specific locus. Chromosomal probes and combinations thereof are chosen for sensitivity and/or specificity when used in the methods. Probe sets can include any number of probes, e.g., at least 2, 3, 4, 5, 6, 7, 8, 9, 10, 15, or 20 probes. The selection of individual probes and probe sets can be performed according to routine in the art, for example as described in US 20060063194, the entire disclosure of which is incorporated by reference. Such selection methods make use of discriminate and/or combinatorial analysis to select probes and probes sets that are useful for copy number profiling of the cancer outcome markers.

Suitable probes for use in in situ hybridization methods according to the present disclosure for the detection of abnormal copy number pattern (aneusomy or polysomy) are a combination of a chromosome enumeration probe and a chromosome locus specific probe hybridizable to at least a portion of the M1 sequence, with each probe labeled to be distinguishable from the other. As is well known in the art, a chromosome enumeration probe can hybridize to a repetitive sequence, located either near or removed from a centromere, or can hybridize to a unique sequence located at any position on a chromosome. For example, a chromosome enumeration probe can hybridize with repetitive DNA associated with the centromere of a chromosome. Centromeres of primate chromosomes contain a complex family of long tandem repeats of DNA comprised of a monomer repeat length of about 171 base pairs, that are referred to as alpha-satellite DNA. A non-limiting example of a specific chromosome enumeration probe is the Vysis CEP® 10 SpectrumGreen probe (Abbott Molecular, Inc., Des Plaines, Ill.). For example, a chromosome 19 enumeration probe is used with a locus specific probe for detecting copy number abnormalities at Chr19, 34.7 Mb-35.6 Mb, for example to determine the status of deletion and/or polysomy of loci contained therein. A locus specific probe hybridizes to a specific, non-repetitive locus on a chromosome, and thus a suitable locus specific probe includes for example at least a portion of any gene contained with M1, for example any portion of the CCNE1 gene. Locus specific probes are available commercially from Abbott Molecular Inc. in a probe set, for example mixed with the Vysis CEP® 10 SpectrumGreen probe.

Probes that hybridize with centromeric DNA are available commercially from Abbott Molecular Inc. (Des Plaines, Ill.) and Molecular Probes, Inc. (Eugene, Oreg.). Alternatively, probes can be made non-commercially using well known techniques. Sources of DNA for use in constructing DNA probes include genomic DNA, cloned DNA sequences such as bacterial artificial chromosomes (BAC), somatic cell hybrids that contain one or a part of a human chromosome along with the normal chromosome complement of the host, and chromosomes purified by flow cytometry or microdissection. The region of interest can be isolated through cloning or by site-specific amplification via the polymerase chain reaction (PCR). See, for example, Nath, et al., Biotechnic Histochem, 1998, 73 (1): 6-22; Wheeless, et al., Cytometry, 1994, 17:319-327; and U.S. Pat. No. 5,491,224. The starting human DNA used to manufacture useful locus specific probes can be obtained by obtaining a nucleic acid sequence for the locus from the Human Genome database, such as that maintained by the University of California Santa Cruz, and then using that sequence to screen in silico a BAC human DNA library, such as that maintained by the Roswell Park Cancer Center or Invitrogen, to identify useful BAC clones. Synthesized oligomeric DNA probes or probes made from nucleic acid analogs, such as peptide nucleic acid (PNA) probes, can also be used.

The size of the chromosomal region detected by the probes used according to the present methods can vary in size, for example, from a short couple hundred base pair probe sequence to a large segment of 900,000 bases. Locus-specific probes that are directly labeled are preferably at least 100,000 bases in complexity, and use unlabeled blocking nucleic acid, as disclosed in U.S. Pat. No. 5,756,696, herein incorporated by reference, to avoid non-specific binding of the probe. It is also possible to use unlabeled, synthesized oligomeric nucleic acid or unlabeled nucleic acid analogs, such as a peptide nucleic acid, as the blocking nucleic acid.

The chromosomal probes can contain any detection moiety that facilitates the detection of the probe when hybridized to a chromosome. Effective detection moieties include both direct and indirect labels as described herein. Examples of detectable labels include fluorophores (i.e., organic molecules that fluoresce after absorbing light), radioactive isotopes (e.g., $^{32}P$, and $^{3}H$) and chromophores (e.g., enzymatic markers that produce a visually detectable marker). Fluorophores are preferred and can be directly labeled following covalent attachment to a nucleotide by incorporating the labeled nucleotide into the probe with standard techniques such as nick translation, random priming, and PCR labeling. Alternatively, deoxycytidine nucleotides within the probe can be transaminated with a linker. The fluorophore can then be covalently attached to the transaminated deoxycytidine nucleotides. See, e.g., U.S. Pat. No. 5,491,224 to Bittner, et al., which is incorporated herein by reference. Useful probe labeling techniques are described in Molecular Cytogenetics: Protocols and Applications, Y.-S. Fan, Ed., Chap. 2, "Labeling Fluorescence In Situ Hybridization Probes for Genomic Targets", L. Morrison et. al., p. 21-40, Humana Press, © 2002, incorporated herein by reference.

Examples of fluorophores that can be used in the methods described herein are: 7-amino-4-methylcoumarin-3-acetic acid (AMCA), Texas Red™ (Molecular Probes, Inc., Eugene, Oreg.); 5-(and-6)-carboxy-X-rhodamine, lissamine rhodamine B, 5-(and-6)-carboxyfluorescein; fluorescein-5-isothiocyanate (FITC); 7-diethylaminocoumarin-3-carboxylic acid, tetramethylrhodamine-5-(and-6)-isothiocyanate; 5-(and-6)-carboxytetramethylrhodamine; 7-hydroxycoumarin-3-carboxylic acid; 6-[fluorescein 5-(and-6)-carboxamido]hexanoic acid; N-(4,4-difluoro-5,7-dimethyl-4-bora-3a,4a diaza-3-indacenepropionic acid; eosin-5-isothiocyanate; erythrosine-5-isothiocyanate; 5-(and-6)-carboxyrhodamine 6G; and Cascade™ blue acetylazide (Molecular Probes, Inc., Eugene, Oreg.). In the preferred probe set, fluorophores of different colors are used such that each chromosomal probe in the set can be distinctly visualized.

After hybridization, the probes can be viewed with a fluorescence microscope and an appropriate filter for each fluorophore, or by using dual or triple band-pass filter sets to observe multiple fluorophores. See, e.g., U.S. Pat. No. 5,776,688 to Bittner, et al., which is incorporated herein by reference. Any suitable microscopic imaging method can be used to visualize the hybridized probes, including automated digital imaging systems, such as those available from MetaSystems or Applied Imaging. Alternatively, techniques such as flow cytometry can be used to examine the hybridization pattern of the chromosomal probes.

Probes can also be labeled indirectly, e.g., with biotin or digoxygenin by means well known in the art. However, secondary detection molecules or further processing are then required to visualize the labeled probes. For example, a probe labeled with biotin can be detected by avidin (e.g. streptavidin) conjugated to a detectable marker, e.g., a fluorophore. Additionally, avidin can be conjugated to an enzymatic marker such as alkaline phosphatase or horseradish peroxidase. Such enzymatic markers can be detected in standard colorimetric reactions using a substrate for the enzyme. Substrates for alkaline phosphatase include 5-bromo-4-chloro-3-indolylphosphate and nitro blue tetrazolium. Diaminobenzidine can be used as a substrate for horseradish peroxidase.

The probes and probe sets useful with the methods can be packaged with other reagents into kits to be used in carrying out the methods herein disclosed.

Preferred Probe Set.

An exemplary probe composition comprises a mixture of directly labeled DNA FISH probes. For example, such a probe set would include a Vysis SpectrumOrange probe and a Vysis SpectrumGreen probe. Suitable probe sets are available commercially premixed in a suitable hybridization buffer.

Preparation of Samples.

A biological sample is a sample that contains cells or cellular material, including cell-containing extracts from a patient sample. For example, lung samples are typically cells or cellular material derived from pulmonary structures, including but not limited to lung parenchyma, bronchioles, bronchial, bronchi, and trachea. Non-limiting examples of biological samples useful for the detection of lung cancer include bronchial specimens, resected lung tissue, lung biopsies, and sputum samples. Examples of bronchial specimens include bronchial secretions, washings, lavage, aspirations, and brushings. Lung biopsies can be obtained by methods including surgery, bronchoscopy, fine needle aspiration (FNA), and transthoracic needle biopsy. In one example, touch preparations can be made from lung biopsies. The inventive assays can also be performed on a circulating tumor cell sample derived from a blood sample from an early stage NSCLC patient. A circulating tumor cell sample can be prepared using the immunomagnetic separation technology available from IMMUNICON®.

Tissues can be fixed with a fixative such as formaldehyde and then embedded in paraffin. Sections are then cut using a microtome and are applied to a microscope slide. Cytology specimens can be prepared from cellular suspensions derived from FNA, bronchial washings, bronchial lavage, or sputum, or disseminated tissue cells. Cytology specimens can be prepared by fixation of cells in ethanol or methanol:acetic acid combined with cytocentrifugation, thin layer deposition methods (e.g. ThinPrep, Cytyc Corp.), smears, or pipetting onto microscope slides. In addition, biological samples can include effusions, e.g., pleural effusions, pericardial effusions, or peritoneal effusions.

Hybridization Methods.

Any suitable in situ hybridization method can be used. Prior to in situ hybridization, chromosomal probes and chromosomal DNA contained within the cell each are denatured. If the chromosomal probes are prepared as a single-stranded nucleic acid, then denaturation of the probe is not required. Denaturation typically is performed by incubating in the presence of high pH, heat (e.g., temperatures from about 70° C. to about 95° C.), organic solvents such as formamide and tetraalkylammonium halides, or combinations thereof. For example, chromosomal DNA can be denatured by a combination of temperatures above 70° C. (e.g., about 73° C.) and a denaturation buffer containing 70% formamide and 2×SSC (0.3M sodium chloride and 0.03 M sodium citrate). Denaturation conditions typically are established such that cell morphology is preserved. For example, chromosomal probes can be denatured by heat, e.g., by heating the probes to about 73° C. for about five minutes.

After removal of denaturing chemicals or conditions, probes are annealed to the chromosomal DNA under hybridizing conditions. "Hybridizing conditions" are conditions that facilitate annealing between a probe and target chromosomal DNA. Hybridization conditions vary, depending on the concentrations, base compositions, complexities, and lengths of the probes, as well as salt concentrations, temperatures, and length of incubation. For example, in situ hybridizations are typically performed in hybridization buffer containing 1-2×SSC, 50-55% formamide, a hybridization acceleratant (e.g. 10% dextran sulfate), and unlabeled blocking DNA to suppress non-specific hybridization. In general, hybridization conditions, as described above, include temperatures of about 25° C. to about 55° C., and incubation lengths of about 0.5 hours to about 96 hours. More particularly, hybridization can be performed at about 32° C. to about 45° C. for about 2 to about 16 hours.

Non-specific binding of chromosomal probes to DNA outside of the target region can be removed by a series of washes with a salt solution. Temperature and concentration of salt in each wash depend on the desired stringency. For example, for high stringency conditions, washes can be carried out at about 65° C. to about 80° C., using 0.2× to about 2×SSC, and about 0.1% to about 1% of a non-ionic detergent such as Nonidet P-40 (NP40). Stringency can be lowered by decreasing the temperature of the washes or by increasing the concentration of salt in the washes.

The hybridization of the probes to the tissue sample can be performed manually, or with the assistance of instruments, such as the ThermoBrite hybridization oven, the VP 2000 Processor, or the XMatrix™ processing instrument (all available commercially from Abbott Molecular, Inc.).

Pre-Selection of Cells.

Cell samples can be evaluated preliminarily by a variety of methods and using a variety of criteria. The probes and methods described herein are not limited to usage with a particular screening methodology. One example is the "scanning method" wherein the observer scans hundreds to thousands of cells for cytologic abnormalities, e.g., as viewed with a DAPI filter. The number of cells assessed will depend on the cellularity of the specimen, which varies from patient to patient. Cytologic abnormalities commonly but not invariably associated with dysplastic and neoplastic cells include nuclear enlargement, nuclear irregularity, and abnormal DAPI staining (frequently mottled and lighter in color). In the scanning step, the observer preferably focuses the evaluation of the cells for chromosomal abnormalities (as demonstrated by FISH) to those cells that also exhibit cytological abnormalities. In addition, a proportion of the cells that do not have obvious cytologic abnormalities can be evaluated since chromosomal abnormalities also occur in the absence of cytologic abnormalities. This scanning method is described in further detail in U.S. Pat. No. 6,174,681 to Halling, et al., which is incorporated herein by reference. Lung cancer cells can be selected for evaluation using the method described in US Patent Pub. 2003/0087248 A1 by Morrison, et al., which is incorporated herein by reference.

Regions of the specimen may also be selected for evaluation using conventional stains, such as stains containing hematoxylin and eosin. For example, a pathologist can stain a section of a paraffin-embedded specimen with a hematoxylin/eosin stain, identify a region as probably cancerous by tissue morphology and staining pattern, and outline that region with a felt tip ink pen or glass scribe. The marked region is then transferred to the corresponding location on a serial section of the paraffin-embedded specimen with a glass scribe, and FISH is performed on that slide. Cells within the scribed region are then evaluated for FISH signals.

Detection of Classification Patterns of Chromosomal Abnormality.

Abnormal cells are characterized by the presence of one or more patterns of chromosomal copy number abnormalities. The presence of a copy number abnormality pattern in a cell in the patient sample is assessed by examining the hybridization pattern of the chromosomal probe (e.g., the number of signals for each probe) in the cell, and recording the number of signals. Aneusomy is typically intended to mean abnormal copy number, either of the whole chromosome or a locus on a chromosome. Abnormal copy number includes both monosomy (one copy) and nullsomy (zero copies) of the autosomes, also referred to as a deletion, and greater than 2 copies, which for a particular chromosomal locus is sometimes referred to as gene amplification (alternatively, amplification is reserved for the situation in which the gene copy number exceeds the copy number of the chromosome in which it is contained). However, sectioning of paraffin-embedded specimens (typically 4-6 μm) may result in truncation of cell nuclei such that the number of FISH signals per cell for some cells will be somewhat lower than the actual number of copies in an intact nucleus. The absolute number of particular FISH probe hybridization signals for each probe is determined and then used in various ratio comparisons.

Test samples can comprise any number of cells that is sufficient for a clinical diagnosis, and in a preferred paraffin-embedded tissue sample, the hybridization pattern is typically assessed in about 20 to about 200 cells. It is preferred to assess the hybridization pattern in about 40 to about 120 cells per sample.

The present disclosure thus describes new findings (DNA copy number gains of M1, a marker region containing cyclin E) that may solve recognized treatment dilemmas by providing methods of determining which patients with early stage disease are at highest risk of disease recurrence or metastasis and who should be definitively treated with drug (or alternatives like radiation) therapies to maximize their chances of long-term survival. In turn, the present disclosure describes findings enabling a specific DNA test that detects a chromosomal copy number gain of a region that includes a nucleotide sequence that encodes cyclin E, a gene whose expression signature has been previously associated with poor cancer patient outcomes. Consequently when a test for cyclin E copy number gain is negative, or normal copy number is present, this identifies patients who have low or no risk of disease recurrence or metastasis who do not need follow-up therapy after resection of their initial tumors. These testing strategies can significantly impact both the morbidity and mortality in patients with early stage NSCLC. The methods used herein also suggest application to other cancers to similarly detect DNA copy number gains of cyclin E that significantly associate with time to disease progression and/or overall survival. As such, the disclosed methods have the potential to solve the question of which early-stage NSCLC patients should receive drug therapy after surgery and can broadly impact cancer treatment decisions and patient outcomes.

Kits.

In another aspect, the present disclosure also provides a kit comprising: a) reagents for determining the presence or absence of a copy number gain for the cyclin E1 gene; and b) instructions for performing the test. In an exemplary embodiment of the kit, the reagents to determine the presence or absence of a copy number gain include detectably-labeled polynucleotides that hybridize to at least a portion of M1 (Chr 19, start position: 34722418; end position 35643933, in human genome assembly hg18 (NCBI Build 36)), which may or may not include any part of that portion of the region that encodes CCNE1. For example, a suitable kit contains any of the above-described probes capable of hybridizing to M1.

Details of the disclosure are further set forth in the following example, which is not intended to limit the scope of the invention as claimed. One of skill in the art will recognize that variations and modifications of the methods may be apparent upon reviewing the instant specification. It is therefore an object to provide for such modifications and variations of the embodiments described herein, without departing from the scope or the spirit of the invention.

Example

Experimental Methods:

Specimens. A total of 178 NSCLC clinically annotated samples were profiled for gene copy number alterations using high-density SNP genotyping microarrays (AFFYMETRIX® 100K array set). All samples were carefully dissected to maximize tumor/normal tissue ratio and verify histopathological type and stage. Only samples from patients with stage I and II disease were analyzed. All of these were from patients treated with surgical resection without any neoadjuvant chemotherapy. Clinical information collected for each patient included race, age, date of birth, sex, clinical stage, pathological stage, location, surgical procedure (SP) date, histology, differentiation, diagnosis date, node positivity, smoking status, chemotherapy status, radiation status, recurrence status, recurrence date, recurrence location, time to recurrence, date of last follow up, status at the last follow up, alive/dead, overall survival and cause of death. Time to Recurrence (TTR) and Overall Survival (OS) were chosen as the parameters of outcome. Other clinical parameters (node status, stage, etc) were considered as confounding variables. Times to recurrence of lung cancer were obtained from the patient charts.

Tables 2 and 3 provide the figures for Overall Survival and Total Time to Recurrence, respectively, for the patient cohort studied.

TABLE 2

| | OS | | |
|---|---|---|---|
| Stage | deaths | alive (censored) | total |
| 1a | 6 | 25 | 31 |
| 1b | 6 | 40 | 46 |

TABLE 2-continued

| | OS | | |
|---|---|---|---|
| Stage | deaths | alive (censored) | total |
| 2a | 0 | 1 | 1 |
| 2b | 7 | 17 | 24 |
| total | 19 | 83 | 102 |

TABLE 3

| | TTR | | |
|---|---|---|---|
| Stage | recurred | recurrence free (censored) | total |
| 1a | 10 | 21 | 31 |
| 1b | 9 | 34 | 43 |
| 2a | 1 | 0 | 1 |
| 2b | 9 | 13 | 22 |
| total | 29 | 68 | 97 |

Copy Number Profiling.

Approximately 30 mg tissue from each tumor was used to extract high molecular weight, genomic DNA using the QIAGEN® DNEASY® kit (QIAGEN®, Valencia, Calif.) following the instructions of the manufacturer. The quality of DNA was checked by agarose gel electrophoresis. Two hundred and fifty nanograms of DNA were processed for hybridization to each of the two micro arrays comprising the GENECHIP® Human Mapping 100K set (Matsuzaki H, Dong S, Loi H, et al. Genotyping over 100,000 SNPs on a pair of oligonucleotide arrays. Nat Methods 2004; 1:109-11) arrays (AFFYMETRIX®, Inc., Santa Clara, Calif.), which covers 116,204 single-nucleotide polymorphism (SNP) loci in the human genome with a mean intermarker distance of 23.6 kb. The microarrays were processed according to recommendations of the manufacturer. Copy number was calculated by comparing the chip signal to the average of 48 normal female samples. Samples with normal tissue contamination were removed by QC.

Statistical Methods.

Univariate analysis was used to test the following parameters as potential confounding factors: Pathological stage, Clinical stage, Smoking status, Age, Sex, Node status, Histology (adenocarcinoma vs squamous cell carcinoma). No significant effects were detected. In survival analysis, interaction of clinical stage and marker regions was tested. No copy number abnormalities had significant interaction with stage (FDR<0.05).

Results:

FIG. 1 is a Kaplan-Meier plot showing the difference in OS between patients with and without amplification (i.e., a copy number gain of at least one) of M1 (Chr 19, start position: 34722418; end position 35643933, in human genome assembly hg18 (NCBI Build 36) for 78 samples. Data for patients with amplification, i.e., a copy number gain of the marker is shown by the lower (darker) line on the plot. Data for patients with the normal baseline complement of two is shown in the upper (lighter) line of the plot. (FDR adjusted p-value=0.0299). Of the 78 samples, a total of 27 showed evidence of amplification of the marker: seventeen had 3 copies, three samples had 4 copies and seven samples had 5 or more copies. The amplified segment is approx. 0.9 Mb long and includes nucleotide sequences containing the Cyclin E1 gene (CCNE1), in addition to: C19orf12 chromosome 19 open reading frame 12, C19orf2 chromosome 19 open reading frame 2, PLEKHF1 (pleckstrin homology domain containing, family F (with FYVE domain) member 1), POP4 processing of precursor 4, ribonuclease P/MRP subunit (*S. cerevisiae*); and ZNF536 zinc finger protein 536. As can be seen from the Kaplan-Meier plot in FIG. 1, amplification, i.e., copy number gains in the marker including CCNE1 are associated with shorter OS in NSCLC stage I-II patients. Table 4 lists overall survival data for several markers including M1 on Chr19. (The marker on Chr6 for which data are shown on the last two lines of Table 4 is shared between different clinical stages).

TABLE 4

Overall Survival for markers including Chr19, 34.7 Mb-35.6 Mb

| Stages | chrom | start. pos | length. seg | FDR | n. amp | mean. amp | n. SNP |
|---|---|---|---|---|---|---|---|
| 1a-2a | 2 | 147604021 | 3513659 | 0.0233 | 7 | 2.8516132 | 166 |
|  | 2 | 159911944 | 1511940 | 0.0001 | 5 | 3.2498274 | 67 |
|  | 2 | 200924525 | 3320890 | 0.0398 | 6 | 3.006085 | 79 |
|  | 2 | 205893481 | 2160144 | 0.0075 | 5 | 2.9990652 | 101 |
|  | 3 | 88399682 | 386599 | 0.0140 | 5 | 3.5534647 | 12 |
|  | 6 | 36255222 | 423122 | 0.0347 | 6 | 2.9201916 | 8 |
|  | 6 | 39088059 | 762306 | 0.0356 | 15 | 3.1071308 | 30 |
|  | 6 | 123724457 | 11850520 | 0.0377 | 7 | 2.9452862 | 667 |
|  | 8 | 4115551 | 55428 | 0.0126 | 7 | 2.8073117 | 19 |
|  | 8 | 6895465 | 1889190 | 0.0166 | 7 | 3.0262839 | 36 |
|  | 11 | 61374252 | 2935902 | 0.0004 | 9 | 3.2120357 | 46 |
|  | 11 | 64310154 | 493823 | 0.0040 | 12 | 3.5343537 | 6 |
|  | 11 | 64803977 | 880941 | 0.0004 | 7 | 3.6506583 | 9 |
|  | 12 | 93683 | 1774306 | 0.0493 | 11 | 3.604318 | 50 |
|  | 17 | 43477124 | 1455714 | 0.0219 | 7 | 3.1622542 | 24 |
|  | 17 | 51532820 | 1678229 | 0.0054 | 10 | 3.1730034 | 54 |
|  | 17 | 69173224 | 2131396 | 0.0304 | 23 | 3.1612824 | 32 |
|  | 19 | 32693527 | 387442 | 0.0183 | 18 | 4.0913848 | 8 |
|  | 19 | 33195577 | 113123 | 0.0459 | 22 | 3.841479 | 6 |
|  | 19 | 34722418 | 921516 | 0.0299 | 27 | 4.1530261 | 20 |
|  | 19 | 38853838 | 1895624 | 0.0085 | 24 | 3.895232 | 34 |
|  | 19 | 57033283 | 5156456 | 0.0091 | 14 | 3.1469281 | 83 |
| 1b-2b | 1 | 109538586 | 1580066 | 0.0224 | 5 | 2.9805551 | 58 |
|  | 6 | 70761833 | 382704 | 0.0116 | 17 | 3.2107404 | 28 |
| 1a-2b | 6 | 70761833 | 382704 | 0.0110 | 24 | 3.0754468 | 28 |

Unlike previously identified predictors (expression signatures), the biomarker M1 described here represents DNA gains (stable events measurable by FISH). FISH probes can be used to enable validation/use of the marker, and the marker is a strong candidate for use as stratification biomarkers in clinical trials. It can be used for example to define molecular subgroups of disease with distinct outcomes. As such it is likely to correlate with drug response.

These data indicate that use of genomic copy number assessment of M1, including the cyclin E1 gene locus measured by FISH, and with use of an appropriate classifier, is of prognostic importance in early stage NSCLC. The classifier was able to produce statistically significant classification of patients who had been treated with surgery without neoadjuvant or follow-up chemotherapy into favorable and unfavorable recurrence categories. No present clinical in vitro diagnostic assay provides this capability. Thus, FISH assays to Chr 19, 34.7 Mb-35.6 Mb, including the genomic sequence for Cyclin E1, performed on early stage NSCLC biopsy specimens or resected tumors appear valuable in decisions related to surgery and adjuvant therapy.

It is to be understood that the foregoing description is intended to illustrate and not limit the scope of the invention. Other aspects, advantages, and modifications of the invention are within the intended scope of the claims set forth below.

What is claimed is:

1. A method of selecting a treatment for a patient suffering from lung cancer, the method comprising the steps of:
    a) providing a test sample from the patient wherein treatment with a chemotherapy agent is at least one treatment option for the patient;
    b) determining a copy number for a marker in the test sample by fluorescent in situ hybridization, wherein the marker comprises cyclin E1 and ZNF536 genes;
    c) comparing the copy number of the marker in the test sample against a normal copy number of the marker, wherein the normal copy number of the marker is two, thereby determining the presence or absence of a copy number gain for the marker in the test sample, and wherein the presence of the copy number gain for the marker is associated with a decreased overall survival time as compared to an overall survival time associated with the absence of the copy number gain for the marker;
    d) selecting a chemotherapy treatment regimen based on the comparison in step c) and
    e) administering adjuvant chemotherapy post-surgery when the comparison in step (c) indicates the subject has a decreased overall survival time,
    wherein the lung cancer is Stage I-II non-small-cell lung cancer.

2. The method of claim 1, wherein the test sample comprises a tissue sample.

3. The method of claim 2, wherein the tissue sample comprises a blood sample, a tumor tissue or a suspected tumor tissue, a thin layer cytological sample, a fine needle aspirate sample, a lung wash sample, a pleural effusion sample, a fresh frozen tissue sample, a paraffin embedded tissue sample or an extract or processed sample produced from any of a peripheral blood sample.

4. The method of claim 2, wherein the tissue sample comprises a lung tissue sample or a peripheral blood sample comprising circulating tumor cells.

5. The method of claim 1, wherein the fluorescent in situ hybridization is performed with a nucleic acid probe that is fluorescently labeled.

6. The method of claim 1, wherein the fluorescent in situ hybridization is performed with at least two nucleic acid probes.

7. The method of claim 1, wherein the fluorescent in situ hybridization is performed with a peptide nucleic acid probe.

8. The method of claim 1, wherein the cancer is selected from the group consisting of squamous cell carcinoma, large cell carcinoma and adenocarcinoma.

9. The method of claim 1, wherein the patient is also being treated with radiation or surgery or a combination thereof.

* * * * *